United States Patent [19]

Che et al.

[11] Patent Number: 4,788,164

[45] Date of Patent: Nov. 29, 1988

[54] INORGANIC-ORGANIC COMPOSITE COMPOSITIONS WITH SUSTAINED RELEASE PROPERTIES

[75] Inventors: Tessie M. Che, Westfield; Dagobert E. Stuetz, Watchung, both of N.J.

[73] Assignee: Hoechst Celanese Corporation, Somerville, N.J.

[21] Appl. No.: 7,548

[22] Filed: Jan. 28, 1987

[51] Int. Cl.$^4$ .............................................. C03C 11/00
[52] U.S. Cl. ....................... 501/39; 501/12; 63/DIG. 2; 428/905; 512/4; 502/407
[58] Field of Search ............... 501/12/39; 502/407, 502/408; 63/DIG. 2; 428/905; 252/522 A; 422/5; 512/4

[56] References Cited

U.S. PATENT DOCUMENTS

| | | | |
|---|---|---|---|
| 195,324 | 9/1877 | Atkinson | 63/DIG. 2 |
| 3,272,646 | 9/1966 | Chopoorian et al. | 501/13 |
| 4,156,067 | 5/1979 | Gould | 252/522 A |
| 4,223,070 | 9/1980 | Hahn et al. | 428/905 |
| 4,447,548 | 5/1984 | Huebsch, III | 501/129 |

FOREIGN PATENT DOCUMENTS

| | | | |
|---|---|---|---|
| 147887 | 7/1985 | European Pat. Off. | 501/12 |
| 2367444 | 5/1978 | France | 63/DIG. 2 |
| 58-213655 | 12/1983 | Japan | 502/407 |
| 59-102833 | 6/1984 | Japan | 501/12 |
| 2038183 | 7/1980 | United Kingdom | 422/5 |
| 2123352 | 2/1984 | United Kingdom | 252/522 A |

*Primary Examiner*—William R. Dixon, Jr.
*Assistant Examiner*—Anthony Green
*Attorney, Agent, or Firm*—Depaoli & O'Brien

[57] ABSTRACT

This invention provides a sustained release composite composition which consists of an inorganic oxide glass monolith with a microporous volume that contains a volatile organic component and a nonvolatile organic component.

In one embodiment the invention provides an article of jewelry which contains an invention composite with a gem-like appearance and a sustained release fragrance.

16 Claims, No Drawings

INORGANIC-ORGANIC COMPOSITE COMPOSITIONS WITH SUSTAINED RELEASE PROPERTIES

BACKGROUND OF THE INVENTION

For many applications it is desirable to provide a composition which is characterized by a sustained release of a fragrance or other volatile organic constituent.

Compositions developed for this purpose include wax pomanders, and inert powders impregnated with essential oils. Polymeric matrices have been substituted for wax as a carrier for fragrance emitting pomanders.

Molded polymeric articles containing entrapped fragrance are described in U.S. Pat. Nos. 3,505,432; 3,553,296; 4,051,159; 4,095,031: 4,110,261; 4,184,099; 4,257,176; and the like; incorporated herein by reference.

Other publications of background interest include U.S. Pat. Nos. 3,926,655; 4,125,478; 4,136,250; 4,293,602; 4,356,115; 4,405,509; 4,528,125; 4,540,721; and 4,584,281; incorporated herein by reference.

Of particular interest with respect to the present invention is prior art which describes slow release of a fragrance from a porous ceramic or glass matrix. Pertinent references include U.S. Pat. Nos. 195,324 and 4,447,548; and Japanese Patent J58213655-A; incorporated herein by reference.

There is continuing interest in the development of new and improved compositions and articles which are characterized by the slow release of a fragrant constituent.

Accordingly, it is an object of this invention to provide novel compositions which exhibit sustained release properties.

It is another object of this invention to provide inorganic-organic composite compositions containing a fragrance component which is slow-released from the composition over an extended period of time.

It is a further object of this invention to provide a fragrant glass monolith with a gem-like appearance.

Other objects and advantages of the present invention shall become apparent from the accompanying description and Examples.

DESCRIPTION OF THE INVENTION

One or more objects of the present invention are accomplished by the provision of a composite composition of an inorganic oxide glass monolith with a microporous structure having an incorporated organic content comprising a volatile organic component and a nonvolatile organic component.

A glass monolith can be molded or machined or otherwise shaped into any desired form as required for specific applications The glass monolith typically is comprised of silica either alone or in combination with up to about 20 weight percent of one or more other inorganic oxides of elements such as lithium, sodium, potassium, rubidium, cesium, magnesium, calcium, strontium, barium, titanium, zirconium, vanadium, tantalum, chromium, molybdenum, tungsten, manganese, iron, nickel, cobalt, copper, zinc, cadmium, boron, aluminum, phosphorus, gallium, germanium, tin, arsenic, antimony, bismuth, selenium, and the like. The glass monolith also can be comprised of alumina, titania or zirconia, or the like, as the main constituent in place of silica.

A present invention glass monolith microporous structure nominally has a pore volume between about 10–80 percent of the total volume, and has pore diameters in the range between about 15–2000 angstroms. The average pore diameter typically is in the range between about 50–300 angstroms.

The organic content can occupy between about 1–99 percent of the microporous volume of the glass monolith, and usually it occupies between about 5–95 percent of the microporous volume.

VOLATILE ORGANIC COMPONENT

The volatile component typically will comprise between about 10–90 weight percent of the organic content which is incorporated in an invention composite composition. The average weight percent normally will be in the range of about 20–60 percent of the organic content.

The term "volatile" as employed herein in reference to an incorporated organic component in an invention composite composition means that at least about 0.1 weight percent of the organic component is released as a vapor from the composite composition over a period of 30 days at 25° C.

In most applications the volatile organic component of an invention composite composition is a fragrance which is slow-released into the environment.

Thus, in another embodiment this invention provides a jewelry article which contains a shaped gem-like composition comprising a composite which consists of an inorganic oxide glass monolith with a microporous structure having an incorporated organic content comprising a volatile fragrance organic component and a nonvolatile organic component.

Most conventional fragrance materials are volatile essential oils. The fragrance can be a synthetically formed material, or a naturally derived oil such as oil of Bergamot, Bitter Orange, Caraway, Cedar Leaf, Cedar Wood, Geranium, Lavender, Orange, Origanum, petitgrain, White Cedar, and the like.

A wide variety of chemicals are known for perfumery, such as aldehydes, ketones, esters, alcohols, terpenes, and the like.

A fragrance can be relatively simple in composition, or can be a complex mixture of natural and synthetic chemical components.

A typical scented oil can comprise woody/earthy bases containing exotic constituents such as sandalwood oil, civet, patchouli oil, and the like. A scented oil can have a light floral fragrance, such as rose extract or violet extract. Scented oil also can be formulated to provide desirable fruity odors, such as lime, lemon or orange.

Synthetic types of fragrance compositions either alone or in combination with natural oils are described in U.S. Pat. Nos. 4,314,915; 4,411,829; and 4,434,306; incorporated herein by reference. Other artificial fragrances include amyl salicylate, citronellol, coumarin, isobornyl acetate, linalool, lyral, phenethyl alcohol, and the like.

A volatile organic component of a present invention composite composition can have utility other than a fragrance. For example, a composite composition can be incorporated in a badge device which is affixed to clothing or the like, and the sustained release volatile organic component in the composite composition can be an insect repellent such as citronellal or N,N-diethyl-m-toluamide. Other applications contemplated include fish lures with a composite composition containing an organic attractant such as oil of anise.

Nonvolatile Organic Component

The nonvolatile organic component typically will comprise between about 10–90 weight percent of the organic content which is incorporated in an invention composite composition.

The term "nonvolatile" as employed herein in reference to an incorporated organic component in an invention composite composition means that essentially zero weight percent of the organic component is released from the composite composition over a period of 30 days at 25° C.

The nonvolatile component can be a mixture of organic materials, e.g., a constituent of the mixture can be an organic dye, such as anthraquinone dye D-16 (B.D.H. Chemicals) or azo dye GR-8 (Japan Photosensitive Pigment Research Institute).

A typical nonvolatile organic component will be an ester; polyol; polyether; hydrocarbon or substituted hydrocarbon; cyclic ketone, lactone or ether; or the like.

One preferred type of nonvolatile organic component is a cyclic polyether such as a monocyclic or polycyclic "crown" ether. Crown ether compounds are disclosed in U.S. Pat. Nos. 3,562,295; 3,860,611; 3,952,015; 3,965,116; 3,966,766; and 4,162,261. A detailed description of the structure and nomenclature of crown ethers is elaborated in chemical literature such as J.A.C.S., 89(10), 2495 (1967), and J.A.C.S., 89(29), 7017 (1967).

Illustrative of suitable crown ethers are those which contain between about 6–15 etheric oxygen atoms contained in a ring, interconnected respectively with alkylene groups containing at least two carbon atoms in series.

A particularly preferred type of nonvolatile organic component is selected from a wide variety of polymers which include polyesters, polyamides, polysiloxanes, polyvinyls, polyoxyalkylenes, polysaccharides, and the like.

Polymers suitable for use as a nonvolatile organic component are described in U.S. Pat. Nos. 3,926,655; 4,051,159; 4,110,261; 4,125,478; 4,136,250; 4,324,703; 4,356,115; 4,405,509; 4,528,125; and 4,540,721; incorporated herein by reference.

Illustrative of the various polymer types are polyethylene, polystyrene, polyvinyl acetate, ethylene vinyl acetate, polyacrylamide, polyacrylonitrile, polymethyl methacrylae, ethylcellulose, hydroxypropylcellulose, nylon-6, guar gum, xanthan gum, and the like.

PREPARATION OF POROUS INORGANIC OXIDE GLASS MONOLITHS

The various methods for the manufacture of porous glass are reviewed in U.S. Pat. No. 4,528,010. The methods include the Vycor (Corning), chemical vapor deposition, white carbon, colloid silica, and silica gel procedures.

One method of producing a porous glass body involves (1) forming an article of desired shape from a parent borosilicate glass; (2) thermally treating the glass article at a temperature of 500°–600° C. to separate the glass into a silica-rich phase and a silica-poor phase; (3) dissolving or leaching the silica-poor phase with acid to provide a porous structure composed of the silica-rich phase; and (4) washing to remove leaching residue, and then drying.

Embodiments for production of porous inorganic oxide glass monoliths by leaching of a soluble phase from a solid glass structure are described in U.S. Pat. Nos. 2,106,744; 2,286,275; 2,303,756; 2,315,328; 2,480,672; 3,459,522; 3,843,341; 4,110,093; 4,112,032; 4,236,930; 4,588,540; and references cited therein; incorporated herein by reference.

U.S. Pat. No. 4,584,280 describes a process for preparing a transparent porous ceramic film which involves applying an anhydrous solution containing an organometallic compound and a multifunctional organic compound to a substrate; and then thermally decomposing the organic compounds.

A more recent development is the "sol-gel" process for preparation of porous monolithic glasses and ceramics at moderate temperatures. The sol-gel procedure involves the formation of a three-dimensional network of metal oxide bonds reaction of metal alkoxides, followed by low temperature dehydration. The resultant porous glass structure optionally can be sintered at elevated temperatures.

In a further embodiment this invention provides a process for producing a sustained release composite composition comprising an inorganic oxide glass monolith with a microporous structure having an incorporated organic content, which comprises (1) hydrolyzing tetraalkoxysilane under acidic or basic pH conditions in a sol-gel reaction medium comprising water and a water-miscible organic solvent component until gellation of the reaction medium is completed; (2) removing the solvent medium to provide a porous glass monolith; and (3) impregnating the porous glass monolith with an organic content comprising a volatile organic component and a nonvolatile organic component.

The impregnation vehicle can be a melt phase of the organic components, or the organic components can be dissolved in a solvent such as ethyl acetate, acetone, methanol, hexane, benzene, chloroform, tetrahydrofuran, N-dimethylformamide, and the like. If a solvent medium is employed, the solvent is removed after the impregnation step is completed.

Embodiments for production of porous inorganic oxide glass monoliths by the sol-gel process are described in U.S. Pat. Nos. 3,640,093; 3,678,144; 3,681,113; 3,811,918; 3,816,163; 3,827,893; 3,941,719; 4,327,065; 4,389,233; 4,397,666; 4,426,216; 4,432,956; 4,472,510; 4,477,580; 4,528,010; 4,574,063; and references cited therein; incorporated herein by reference. Mat. Res. Soc. Symp. Proc., 73, 35 (1986) by Hench et al describes the role of chemical additives in sol-gel processing; incorporated herein by reference.

Illustrative of water-miscible solvents employed in a sol-gel process embodiment are alkanols such as methanol and ethanol; ketones such as acetone and methyl ethyl ketone; esters such as methyl acetate and ethyl formate; ethers such as dioxane and tetrahydrofuran; amides such as dimethylformamide, dimethylacetamide and 1-methyl-2-pyrrolidinone; and the like.

Acidic pH conditions in the sol-gel process can be provided by the addition of mineral acids such as hydrochloric acid; and basic pH conditions can be provided by the addition of bases such as ammonium hydroxide.

Illustrative of tetraalkoxysilanes and other metal and metalloid alkoxides are methoxy and ethoxy derivatives of silicon, lithium, magnesium, titanium, manganese, aluminum, tin, antimony, and the like. Aryloxy derivatives also can be utilized in the sol-gel process.

Porous glass monoliths produced by a sol-gel process embodiment have an advantageous combination of properties, and generally have a superior transparent or translucent appearance as compared to porous glass monoliths prepared by other techniques, e.g., by the leaching of a silica-poor phase from a borosilicate glass.

A sol-gel derived porous glass monolith is homogeneous, and the inorganic matrix can be obtained essentially free of inorganic or organic impurities, e.g., less than 2 weight percent of impurities.

A sol-gel derived porous glass monolith typically has a pore structure in which substantially all of the pores have diameters within about a 100 angstrom diameter variation range, e.g., within a range between about 50–150 or 300–400 or 900–1000 angstroms, as determined by sol-gel processing conditions.

A sol-gel derived porous glass monolith of a present invention inorganic-organic composite can have exceptional properties because the inorganic matrix is homogeneous in chemical composition and physical structure, and the control of the sustained release function of a composite composition is facilitated.

SUSTAINED RELEASE PROPERTIES

A present invention composite composition has a of features which provide exceptional sustained release properties.

The glass monolith structure has a relatively large pore volume (e.g., up to 80 percent of the total volume), and can absorb a high level of organic components.

There are several factors which contribute to the sustained release of a volatile organic component over an extended period of time (e.g., 3–15 months) from a composite composition.

The average pore diameter of a typical glass monolith structure is in the range between about 50–300 angstroms, and the pore diameters are substantially uniform with a narrow slow-release of the volatile organic component at a relatively constant rate.

If the volatile organic component is a solute in a solid solution with the nonvolatile organic component, the volatile component diffuses and migrates at a relatively constant rate to the outer surface and evaporates into the environment.

If the volatile organic component is a separate phase from the nonvolatile organic component, the volatile component migrates by capillary action between the interfaces of the nonvolatile organic component and the interior surfaces of the glass monolith pores. The nonvolatile organic component can have a microporous structure which has a content of immiscible volatile organic component.

Another degree of sustained rate of release can be accomplished by coating the surface of the composite composition with a thermoplastic polymer such as poly(methyl methacrylate), polyvinyl acetate or hydroxyethylcellulose. The thickness of this secondary diffusion barrier and the degree of microporosity if any will determine the rate of evaporation of the volatile organic component through the barrier.

More than one of each of the volatile and nonvolatile components can be utilized in the organic content, and additional organic components can be included such as dyes, anti-oxidants, ultraviolet stabilizers, and the like.

The following examples are further illustrative of the present invention. The components and specific ingredients are presented as being typical and various modifications can be derived in view of the foregoing disclosure within the scope of the invention.

EXAMPLE I

A reactor is charged with 80 g of diced Versamid 930 (General Mills), and the polyamide is heated to melting temperature (about 135° C).

A 20 g quantity of Volatile Fragrance Oils (Spring Flower #754; International Fragrance and Flavors Co.) is added to the polyamide melt with stirring.

Two sections of porous glass (3 cm × 3 cm × 1 cm) of 40–50 angstroms average diameter are submerged in the heated solution of polyamide and fragrance, and the reactor is sealed and pressured with nitrogen to reduce vaporization of the fragrance from the solution.

After a period of about two hours, the impregnated porous glass sections are removed from the liquid phase in the reactor.

One of the porous glass sections then is film coated with poly(methyl methacrylate) by dipping the glass section into a methyl ethyl ketone solution of poly(methyl methacrylate), and then air drying.

After six months, there is sustaining release of fragrance from both glass composite compositions. After one year, the release of fragrance is still detectable from the glass composite composition which is coated with poly(methyl methacrylate).

EXAMPLE II

A starting solution for the production of thin films is prepared by admixing 50 ml of ethanol, 50 ml of dioxane, 10 ml of tetramethoxysilane, 5 ml of 0.01 N HCl, 3 g of methylcellulose and 0.5 g of lavender oil. The solution is allowed to stand for two hours at room temperature.

Glass slides are dipped into the solution, and then dried at 50° C. for 10 hours. The resultant transparent film coating is a porous silicate monolith containing a pore volume encapsulated content of polymers and fragrance components.

In an alternative procedure, the fragrance component is not included in the film preparation solution. After glass slides are coated with porous silicate film, the glass slides are dipped into an alcohol solution of lavender oil to impregnate the porous film coating with the solution. After glass slides are dried to remove the solvent, the resultant composite coating on the glass slides is a transparent silicate film with a microporous structure containing incorporated polymer and fragrance components.

EXAMPLE III

A 1.627 gram piece of porous glass, with a stoichiometric composition of $Be_3Al_2(Si_6O_{18})Cr_{0.1}$, a pore size distribution ranging from 100–200 Å and an open pore volume of 30% of the total bulk volume, is cut and polished such that the resultant piece has the visual characteristics of a beryl gem such as an emerald.

Under evacuation, the cut glass is immersed in a solution containing 60% glycerol, 35% ethanol and 5% 6-methylionone (irone - fragrance of violets). The final weight of the completely infiltrated piece is 3.5 g. The sustained release weight loss over a period of one month is 0.04 g.

EXAMPLE IV

A 1 gram piece of porous $SiO_2$ glass, with a pore size distribution of 250–350 Å and an open pore volume of about 50% of the total bulk volume, is cut and polished in the shape of an opal gem. The porous glass is immersed in an aqueous/ethanolic (50:50) solution containing 5 wt % methylcellulose+1% 3-methyl-2-(2-pentenyl)-2-cyclopenten-1-one (jasmone - odor of jasmine). The final weight of the completely infiltrated composite is 2 grams. The sustained release weight loss over a period of one month is 0.01 g.

EXAMPLE V

A 2 gram piece of porous glass, with the stoichiometric composition of zircon ($ZrSiO_4$), a pore size distribution range of 50–150 Å, and an open pore volume of 65% of the total bulk volume, is cut and polished in the form of a diamond gem. The porous glass is immersed in a solution containing 2 weight percent linalool and 15 weight percent methyl acetylsalicylate in glycerol.

After the glass is fully impregnated with the perfume-fixative glycerol mixture, it is soaked in absolute ethanol for 15 minutes. The impregnated glass is then dipped in a solution of 10:1 polydimethylvinylsiloxane oligomer end-capped with propoxide groups/polymethylhydrodimethylsiloxane oligomer, which additionally contains 1.0% by weight of $H_2PtCl_4$ catalyst (Petrarch Catalog PS 273). The glass is immersed for one-half hour in the solution. The glass then is removed from the solution, placed in a closed container, and the coating is cured at room temperature for a 72 hour period.

EXAMPLE VI

The porous glass described in Example V is immersed in a solution of 5 weight percent linalool and 3 weight percent diisopropylperoxydicarbonate (free radical initiator) in diethylene glycol bis(allyl carbonate) monomer (Akzo Chem Nouryset 200). Slow polymerization of the monomer is induced by heating the system at 50° C. under 200 psig ($N_2$) for 24 hours. The temperature is then ramped 10° C. per hour to 100° C., and held at 100° C. for 2 hours to obtain a fully cured polymer/fragrance/glass composite. Excess polymer is trimmed away from the composite to provide the original diamond shape, and the composite is polished to a gem-like appearance.

What is claimed is:

1. A sustained release composite composition of an inorganic oxide glass monolith with a microporous structure and a physically incorporated organic content consisting essentially of (1) between about 10–90 weight percent, based on the incorporated organic content, of volatile organic component selected from the group consisting of fragrances and insect repellents; and (2) a nonvolatile organic component selected from the group consisting of esters, polyols, polyethers, hydrocarbons or substituted hydrocarbons, cyclic ketones, cyclic lactones, cyclic ethers, and polymers.

2. A composite composition in accordance with claim 1 wherein the inorganic oxide comprises silica, alumina, titania or zirconia.

3. A composite composition in accordance with claim 1 wherein the inorganic oxide comprises a mixture of silica and at least one additional inorganic oxide.

4. A composite composition in accordance with claim 1 wherein the glass monolith microporous structure has pore diameters in the range between about 15–2000 angstroms.

5. A composite composition in accordance with claim 1 wherein between about 5–95 percent of the glass monolith microporous structure volume is filled with the incorporated organic content.

6. A composite composition in accordance with claim 1 wherein the composite has a gem appearance.

7. A sustained release composition of an inorganic oxide glass monolith with a microporous structure and a physically incorporated organic content consisting essentially of (1) between about 10–90 weight percent, based on the incorporated organic content, of a volatile organic component selected from the group consisitng of fragrances and insect repellents; and (2) a nonvolatile polymer component selected from the group consisting of polyesters, polyamides, polysiloxanes, polyvinyls, polyoxyalkylenes, and polysaccharides.

8. A composite composition in accordance with claim 7 wherein the volatile organic component and the nonvolatile polymer component are miscible and are in the form of a solid solution.

9. A composite composition in accordance with claim 7 wherein the volatile organic component and the nonvolatile polymer component are immiscible and are in the form of two separate organic phases.

10. A composite composition in accordance with claim 7 wherein the organic content contains a nonvolatile organic dye as an additional component.

11. A composite composition in accordance with claim 7 wherein the composite is transparent or translucent.

12. A composite composition in accordance with claim 7 wherein the composite has a gem appearance and is in the form of a jewelry article.

13. A composite composition in accordance with claim 7 wherein the composite has a polymer surface coating.

14. A process for producing a sustained release composite composition consisting essentially of an inorganic oxide glass monolith with a microporous structure and an incorporated organic content, which comprises (1) hydrolyzing tetraalkoxysilane under acidic or basic pH conditions in a sol-gel reaction medium comprising water and a water-miscible organic solvent component until gellation of the reaction medium is completed; (2) removing the solvent medium to provide a porous glass monolith; and (3) impregnating the porous glass monolith with an organic content consisting essentially of (1) between about 10–90 weight percent, based on the incorporated organic content, of volatile organic component selected from the group consisting of fragrances and insect repellents; and (2) a nonvolatile organic component selected from the group consisting of esters, polyols, polethers, hydrocarbons or substituted hydrocarbons, cyclic ketones, cyclic lactones, cyclic ethers, and polymers.

15. A composite composition in accordance with the process of claim 14.

16. A jewelry article which contains a shaped composition with a gem appearance comprising a sustained release composite which consists of an inorganic oxide glass monolith with a microporous structure and a physically incorporated organic content consisting essentially of (1) between about 10–90 weight percent, based on the incorporated organic content, of a volatile fragrance organic component; and (2) a nonvolatile organic component selected from the group consisting of esters, polyols, polyethers, hydrocarbons or substituted hydrocarbons, cyclic ketones, cyclic lactones, cyclic ethers, and polymers.

* * * * *